United States Patent
Krueger et al.

(10) Patent No.: US 6,443,910 B1
(45) Date of Patent: Sep. 3, 2002

(54) BONE MARROW BIOPSY NEEDLE

(75) Inventors: John A. Krueger, Milwaukee; Grant A. Clark, Bristol, both of WI (US)

(73) Assignee: Allegiance Corporation, McGaw Park, IL (US)

( * ) Notice: Subject to any disclaimer, the term of this patent is extended or adjusted under 35 U.S.C. 154(b) by 0 days.

(21) Appl. No.: 09/552,444

(22) Filed: Apr. 18, 2000

(51) Int. Cl.$^7$ ................................................ A61B 10/00
(52) U.S. Cl. ........................................................ 600/567
(58) Field of Search .............................. 600/564, 565, 600/566, 567; 604/158, 159, 160, 161, 162, 163, 164, 164.01, 164.11; 606/167, 170

(56) References Cited

U.S. PATENT DOCUMENTS

| | | |
|---|---|---|
| 2,219,605 A | 10/1940 | Turkel |
| 2,827,039 A | 3/1958 | Seiger |
| 3,007,471 A | 11/1961 | McClure, Jr. |
| 3,570,498 A | 3/1971 | Weighton |
| 3,606,878 A | 9/1971 | Kellogg, Jr. |
| 3,844,272 A | 10/1974 | Banko ................... 128/2 B |
| 3,882,849 A | 5/1975 | Jamshidi ................ 128/2 B |
| 3,995,619 A | 12/1976 | Glatzer ................. 128/2 B |
| 4,010,737 A | 3/1977 | Vilaghy et al. ......... 128/2 B |
| 4,013,080 A | 3/1977 | Froning ................. 128/347 |
| 4,096,860 A | 6/1978 | McLaughlin ........... 128/214.4 |
| 4,356,828 A | 11/1982 | Jamshidi ................ 128/754 |
| 4,396,021 A | 8/1983 | Baumgartner .......... 128/754 |
| 4,403,617 A | 9/1983 | Tretinyak ............... 128/754 |
| 4,461,305 A | 7/1984 | Cibley ................... 128/754 |
| 4,469,109 A | 9/1984 | Mehi ..................... 128/754 |
| 4,487,209 A | 12/1984 | Mehi ..................... 128/754 |
| 4,543,966 A | 10/1985 | Islam et al. ............ 128/754 |
| 4,619,272 A | 10/1986 | Zambelli ............... 128/753 |
| 4,630,616 A | 12/1986 | Tretinyak .............. 128/753 |
| 4,643,196 A | 2/1987 | Tanaka et al. .......... 128/753 |

(List continued on next page.)

FOREIGN PATENT DOCUMENTS

| | | |
|---|---|---|
| RU | 483978 | 12/1975 |
| RU | 567447 | 8/1977 |
| WO | WO 97/32524 | 9/1997 |
| WO | WO 00/10465 | 8/1999 |

OTHER PUBLICATIONS

Marketing Literature, "Bone/Bone Marrow Biopsy Set with Extraction Cannula", MD Tech, 8/98.

Marketing Literature, Ranfac's Bone Marrow Biopsy Needles 1994.

Allegiance Corporation Marketing Literature, Bone and Bone Marow Biopsy Devices 11/95.

*Primary Examiner*—Kevin Shaver
*Assistant Examiner*—Pamela Wingood
(74) *Attorney, Agent, or Firm*—Andrew G. Rozycki

(57) ABSTRACT

The present invention provides a bone marrow biopsy device 10 that includes a handle 12, an outer cannula 16, a stylet 14, and an inner member 18. The outer cannula 16 is secured in the handle 12. The outer cannula defines a distal tip 29 that is tapered to provide a distal cutting edge. The stylet 14 is designed to be inserted in the outer cannula 16. The stylet defines a sharp distal tip 30. The inner member 18 is designed to be inserted in the outer cannula 16. The inner member 18 defines a cuffing finger 45.

19 Claims, 6 Drawing Sheets

U.S. PATENT DOCUMENTS

| | | | |
|---|---|---|---|
| 4,649,918 A | 3/1987 | Pegg et al. | 128/305 |
| 4,681,123 A | 7/1987 | Valtchev | 128/753 |
| 4,682,606 A | 7/1987 | DeCaprio | 128/754 |
| 4,699,154 A | 10/1987 | Lindgren | 128/754 |
| 4,702,260 A | 10/1987 | Wang | 128/753 |
| 4,708,147 A | 11/1987 | Haaga | 128/753 |
| 4,747,414 A | 5/1988 | Brossel | 128/754 |
| 4,766,907 A | 8/1988 | DeGroot et al. | 128/754 |
| 4,774,948 A | 10/1988 | Markham | 128/329 |
| 4,785,826 A | 11/1988 | Ward | 128/754 |
| 4,790,329 A | 12/1988 | Simon | 128/749 |
| 4,793,363 A | 12/1988 | Ausherman et al. | 128/754 |
| 4,799,494 A | 1/1989 | Wang | 128/753 |
| 4,799,495 A | 1/1989 | Hawkins et al. | 128/754 |
| 4,817,631 A | 4/1989 | Schnepp-Pesch et al. | 128/753 |
| 4,838,282 A | 6/1989 | Strasser et al. | 128/754 |
| D303,009 S | 8/1989 | Strasser et al. | D24/24 |
| 4,922,602 A | 5/1990 | Mehi | 29/460 |
| 4,931,059 A | 6/1990 | Markham | 606/185 |
| 4,953,558 A | 9/1990 | Akerfeldt | 128/751 |
| 4,958,625 A | 9/1990 | Bates et al. | 128/751 |
| 4,986,279 A | 1/1991 | O'Neill | 128/754 |
| 5,012,818 A | 5/1991 | Joishy | 128/754 |
| 5,027,827 A | 7/1991 | Cody et al. | 128/753 |
| 5,031,634 A | 7/1991 | Simon | 128/754 |
| 5,036,860 A | 8/1991 | Leigh et al. | 128/754 |
| 5,040,542 A | 8/1991 | Gray | 128/754 |
| 5,080,655 A | 1/1992 | Haaga | 604/265 |
| 5,127,916 A | 7/1992 | Spencer et al. | 606/185 |
| 5,172,701 A | 12/1992 | Leigh | 128/753 |
| 5,172,702 A | 12/1992 | Leigh et al. | 128/754 |
| 5,195,988 A | 3/1993 | Haaga | 604/265 |
| 5,224,470 A | 7/1993 | Schnepp-Pesch et al. | 128/753 |
| 5,257,632 A | 11/1993 | Turkel et al. | 128/754 |
| 5,279,306 A | 1/1994 | Mehl | 128/753 |
| 5,284,156 A | 2/1994 | Schramm et al. | 128/754 |
| 5,318,543 A * | 6/1994 | Ross et al. | 604/167 |
| 5,333,619 A | 8/1994 | Burgio | 128/754 |
| 5,341,816 A | 8/1994 | Allen | 128/754 |
| 5,348,022 A | 9/1994 | Leigh et al. | 128/753 |
| 5,357,974 A | 10/1994 | Baldridge | 128/754 |
| 5,368,045 A | 11/1994 | Clement et al. | 128/754 |
| 5,385,151 A | 1/1995 | Scarfone et al. | 128/754 |
| 5,394,887 A | 3/1995 | Haaga | 128/754 |
| 5,429,138 A | 7/1995 | Jamshidi | 128/753 |
| 5,449,001 A | 9/1995 | Terwilliger | 128/754 |
| 5,462,062 A | 10/1995 | Rubinstein | 128/754 |
| 5,476,101 A | 12/1995 | Schramm et al. | 128/754 |
| 5,476,102 A | 12/1995 | Como et al. | 128/754 |
| 5,477,862 A | 12/1995 | Haaga | 128/754 |
| 5,507,298 A | 4/1996 | Schamm et al. | 128/754 |
| 5,522,398 A | 6/1996 | Goldenberg et al. | 128/754 |
| 5,526,821 A | 6/1996 | Jamshidi | 128/753 |
| 5,595,186 A | 1/1997 | Rubinstein et al. | 128/754 |
| 5,615,690 A | 4/1997 | Giurtino et al. | 128/754 |
| 5,634,473 A | 6/1997 | Goldenberg et al. | 128/754 |
| 5,713,368 A | 2/1998 | Leigh | 128/753 |
| 5,718,237 A | 2/1998 | Haaga | 128/751 |
| 5,807,277 A | 9/1998 | Swaim | 600/567 |
| 5,823,970 A | 10/1998 | Terwilliger | 600/564 |
| 5,833,628 A | 11/1998 | Yaun et al. | 600/567 |
| 5,843,001 A | 12/1998 | Goldenberg | 600/567 |
| 5,868,684 A | 2/1999 | Akerfeldt et al. | 600/564 |
| 5,885,226 A | 3/1999 | Rubinstein et al. | 600/564 |
| 5,910,121 A | 6/1999 | Paolo et al. | 600/562 |
| 6,007,496 A | 12/1999 | Brannon | 600/565 |

* cited by examiner

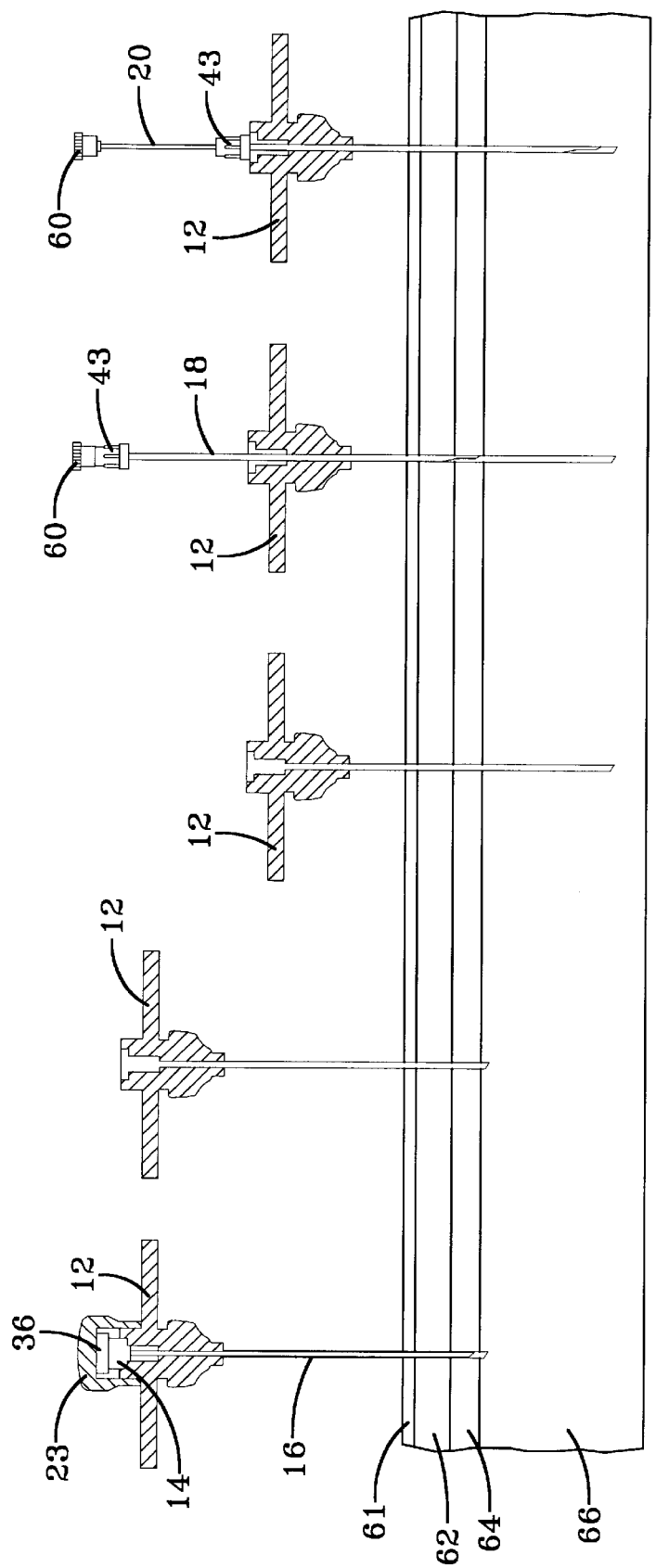

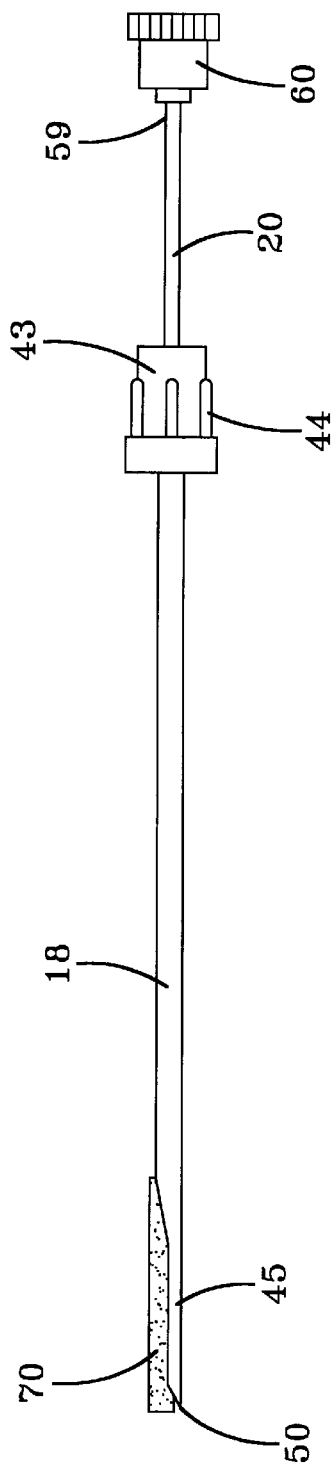
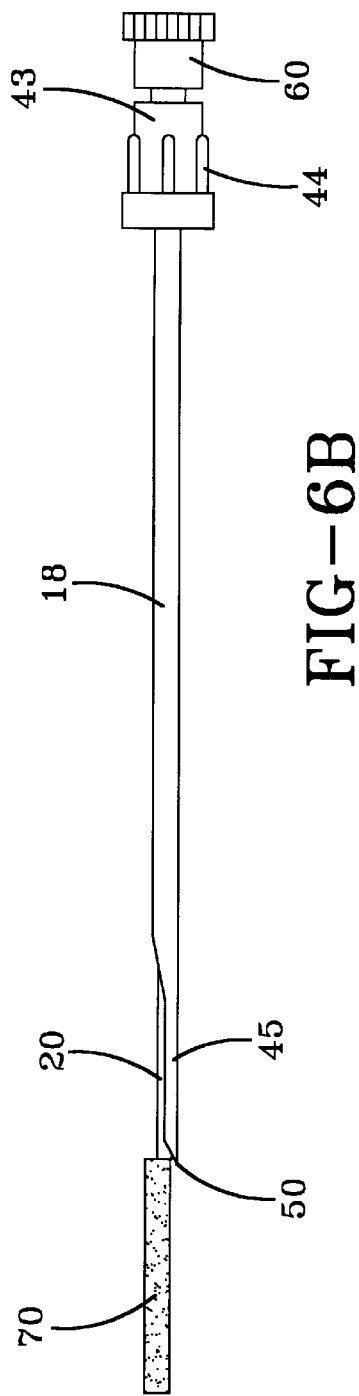
FIG-6A
FIG-6B

BONE MARROW BIOPSY NEEDLE

TECHNICAL FIELD OF THE INVENTION

The present invention relates to medical instruments utilized in securing marrow tissue samples from bone structures.

BACKGROUND OF THE INVENTION

A biopsy medical instrument is an instrument which is designed to take samples of tissue. Typically, a biopsy device that is utilized to obtain samples from the bone consists of a hollow cannula that is surrounding a stylet. The stylet includes a sharp distal tip which extends outwardly from the cannula when the stylet is secured inside the cannula. The combined cannula and stylet is used to penetrate through the outer layer of the bone, called the cortex, which is considerably harder than the trasecular bone layer and the tissue within the bone that is sampled, referred to as the marrow. Once the stylet and cannula have penetrated the cortex, the stylet is removed and the cannula is extended further into the medular cavity, thereby capturing marrow tissue for a sample.

The architecture of the tissue sample that is removed by the biopsy device is critical in several respects. Initially, the size of the sample is important, with larger tissue sample sizes representing better samples for subsequent testing to be performed on the tissue. However, the larger the cannula and stylet that are inserted into the bone, the more pain is generated at the site of the penetration for the patient. In addition, it is important that the sample be taken without damaging the marrow tissue. However, in removing the tissue sample the tissue must be excised from the remaining tissue. This removal can result in compromising the tissue sample by damaging the tissue sample.

Several approaches have been taken to secure large, undamaged tissue samples using bone marrow biopsy devices. However, each of these approaches has significant drawbacks which limit commercial and clinical usefulness. For example, one such approach utilizes suction provided at the proximal end of the cannula. The suction is designed to pull the tissue sample into the cannula and retain the tissue sample inside the cannula. While in theory such suction would help secure larger tissue samples, in practice exposure to such suction forces results in damage to the marrow tissue when the sample is removed from the patient.

Another approach utilizes a snare in the form of a coil at the distal end of the cannula. When rotated, the coil decreases in diameter to secure the biopsy tissue sample in the cannula. While again in theory such a device would help secure larger tissue samples, in practice it subjects the tissue sample to compression forces which causes damage to the sample.

Other approaches include the use of inwardly projecting members such as scallops within the cannula. The theory behind such devices is that when the tissue sample is inserted into the cannula, the inward direction of the scallops allows the tissue sample to slide over such projecting members but when the tissue sample is removed from the patient the projecting members latch onto the tissue sample to secure the tissue sample in the cannula. Again, however, this theory fails in practice as it causes trauma to the tissue when the tissue sample is removed from the patient.

Other approaches include providing apertures on the side of the cannula which, in theory, allow tissue to expand into such apertures to help secure the tissue sample in the cannula. Likewise, one approach utilizes a screw member in the cannula which is designed to urge the tissue inwardly and retain the tissue sample in of the cannula. Once again, providing a cavity for the tissue sample that is not smooth results in damage to the tissue when the tissue sample is removed from the patient.

Yet another approach at securing the biopsy sample within the cannula involves the use of a pair of coaxial cannulas. One of the two cannulas includes a curved section that acts as a cam to compress the inner cannula around the tissue sample when the inner cannula is withdrawn from the outer cannula. Once again, in theory this would help to secure the tissue within the cannula, but in practice it subjects the tissue sample to such compression forces that damage to the sample is caused. In addition, the use of dual cannulas acts to either decrease the size of the tissue sample or to increase the size of the biopsy device causing increased pain to the patient. A similar approach utilizes an additional coaxial hollow cannula designed to sheer or cut-off the tissue when the two cannulas are rotated relative to each other. However, because such devices require additional hardware in the cannula, either the size of the tissue sample is decreased or the size of the biopsy device is increased.

What would be desirable is a bone marrow biopsy device that is able to secure a large tissue sample while avoiding increasing the size of the biopsy device thereby minimizing the pain experienced by the patient during such procedure. Such a device would also avoid subjecting the tissue sample to undue forces, whether such forces be compression, suction, etc., to remove the tissue sample without causing undue damage to the tissue following removal of the sample from the patient.

SUMMARY OF THE INVENTION

The present invention is able to secure a large tissue sample while avoiding increasing the size of the biopsy device thereby minimizing the pain experienced by the patient during such procedure. The present invention further avoids subjecting the tissue sample to undue forces, whether such forces be compression, suction, etc., thus reducing damage to the tissue following removal of the sample from the patient.

The present invention provides a bone marrow biopsy device that includes a handle, an outer cannula, a stylet, and an inner member. The outer cannula is secured in the handle. The outer cannula defines a distal tip that is tapered to provide a distal cutting edge. The stylet is designed to be inserted in the outer cannula. The stylet defines a sharp distal tip. The inner member is designed to be inserted in the outer cannula. The inner member defines a cutting finger.

Thus, there is disclosed a bone marrow biopsy device comprising a handle; an outer cannula secured in the handle, the outer cannula defining a distal tip that provides a distal cutting edge; a stylet designed to be inserted in the outer cannula, the stylet defining a sharp distal tip; and an inner member designed to be inserted in the outer cannula, the inner member defining a cutting finger.

Thus, there is further disclosed a member for use with a bone marrow biopsy device comprising a proximal end formed with a hub that secures the member; and a distal end that defines a cutting finger.

There is further disclosed a kit for use in obtaining a bone marrow biopsy comprising a handle having an outer cannula secured therein, the outer cannula defining a distal tip that provides a distal cutting edge; a stylet designed to be inserted in the outer cannula, the stylet defining a sharp distal tip; and an inner member designed to be inserted in the outer cannula, the inner member defining a cutting finger.

There is disclosed a method for sampling bone marrow tissue comprising: inserting a stylet into an outer cannula; penetrating the bone cortex with the stylet and the outer cannula; removing the stylet; further inserting the outer cannula into a medular cavity, thereby trapping bone marrow tissue within the outer cannula; extending an inner member into the outer cannula, the inner cannula defining a cutting finger; rotating the inner member to shear off the specimen with the cutting finger; and removing the specimen from the patient.

BRIEF DESCRIPTION OF THE DRAWINGS

FIG. 5 is a cross-sectional elevational view showing the use of the biopsy device of FIGS. 1 through 3.

FIG. 6A is a close up view of the inner member and the ejector pin of FIGS. 1 and 2 with the tissue sample in the inner member.

FIG. 6B is a close up view of the inner member and the ejector pin of FIGS. 1 and 2 with the tissue sample removed from the inner member.

DETAILED DESCRIPTION OF A PREFERRED EMBODIMENT

Figure 1:
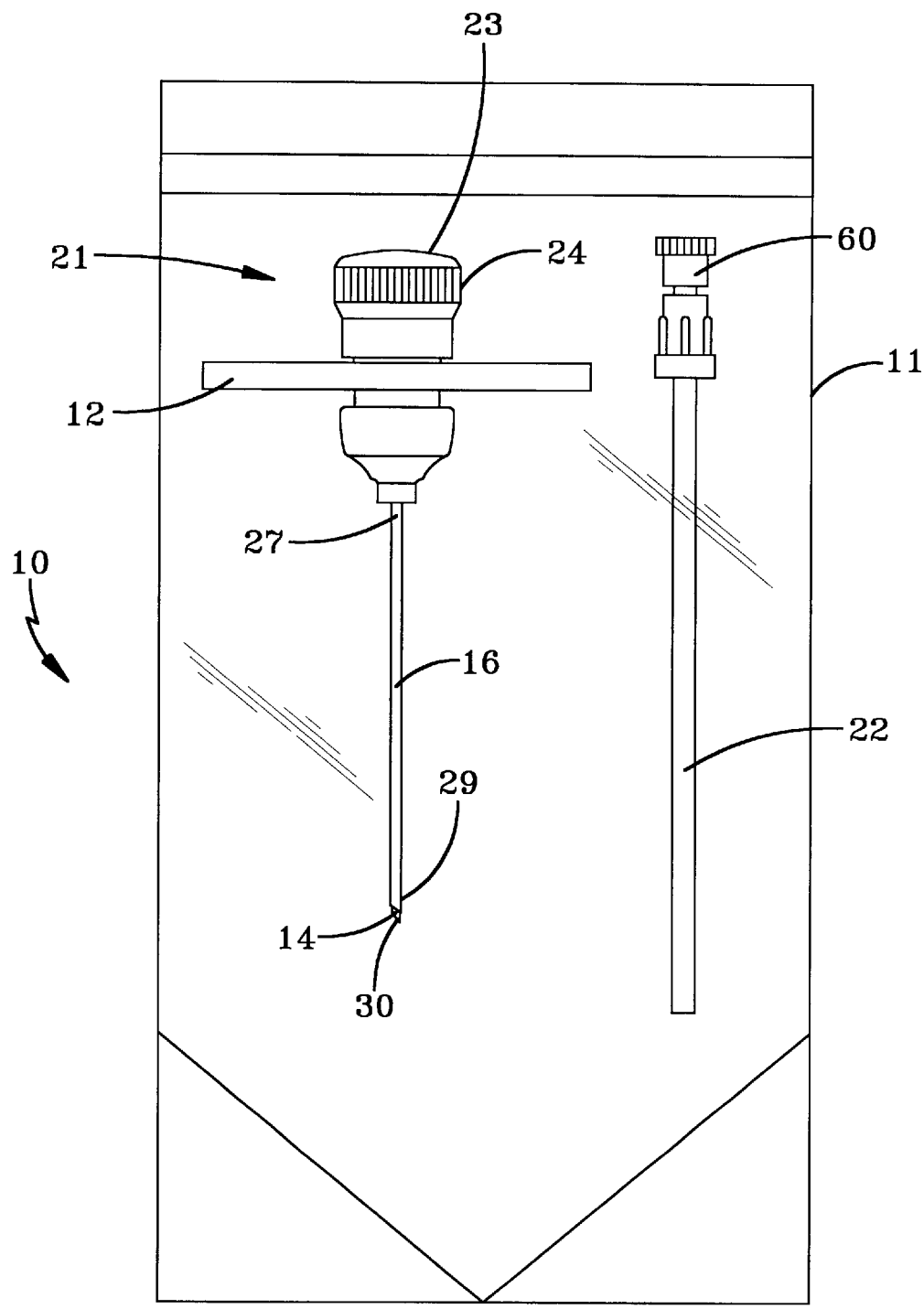
FIG. 1 is an elevational view of an outer cannula and an inner cannula in accordance with the principles of the present invention in the form of a kit packaged in a container.

Referring first to FIG. 1, a bone marrow biopsy device made in accordance with the principles of the present invention in a package is generally designated by the reference number 10. A bone marrow biopsy device 10 made in accordance with the principles of the present invention includes a handle 12, a stylet 14, an outer cannula 16, an inner member 18, an ejector pin 20, and a protective sheath 22. The bone marrow biopsy device 10 made in accordance with the principles of the present invention is preferably provided to the user sterile in a package 11.

Because the bone marrow biopsy device 10 made in accordance with the principles of the present invention must be inserted through the hard outer cortex layer of a bone, the handle 12 is designed to ergonomically nest in the palm of a health care professional. Thus, a proximal portion 21 of the handle 12 includes a tapered cap 23 designed to fit into the middle portion of the palm. The tapered cap 23 is adapted to engaged to the handle 12. In a preferred embodiment, the tapered cap 23 is threadingly engaged to cooperating threads on the handle 12. In addition, the tapered cap 23 may include a scored outer surface top 24 to assist the health care professional is securing and removing the cap 23.

The handle 12 is designed so that the outer cannula 16 extends between the index and the middle finger of the health care professional. This allows the health care professional to exert a great deal of pressure on the handle 12 from the palm of the hand. This further allows the health care professional to direct the device 10 into the patient utilizing the fingers that are wrapped around the handle 12. In a preferred embodiment, the handle 12 is molded from a hard plastic.

The bone marrow biopsy device 10 made in accordance with the principles of the present invention includes an outer cannula 16. The outer cannula 16 is permanently secured at a proximal end 27 to the handle 12. The distal tip 29 of the outer cannula 16 is tapered to provide a distal cutting edge, best seen in FIG. 2A. The outer cannula 16 is preferably designed of a hard material to withstand the forces applied on the outer cannula 16 when penetrating through the cortex of the bone. Thus, in a preferred embodiment the outer cannula 16 is made of stainless steel.

Figure 2A:
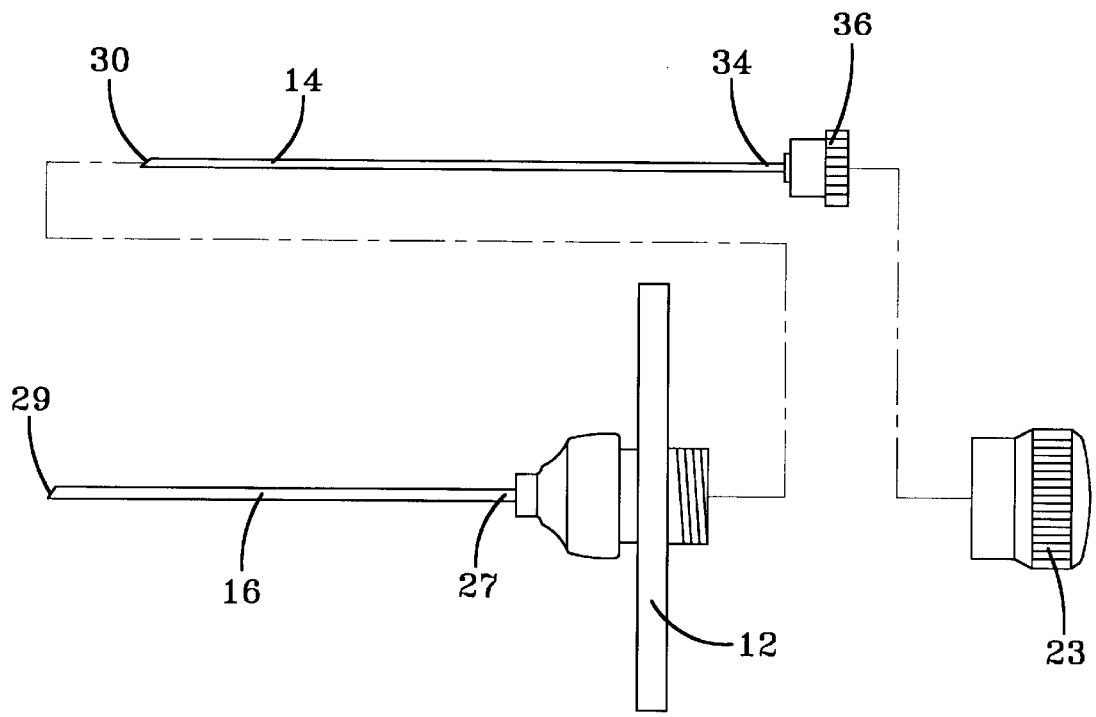
FIG. 2A is a perspective, exploded view of the handle including the outer cannula, the cap and the stylet of the bone marrow biopsy device of FIG. 1.

The bone marrow biopsy device 10 made in accordance with the principles of the present invention also includes a stylet 14, best seen in FIG. 2A. The stylet 14 includes a sharp distal tip 30 designed to penetrate the hard cortex layer of a bone. Like the outer cannula 16, the stylet 14 is preferably designed of a hard material to withstand the forces applied on the stylet 14 when penetrating through the cortex of the bone, such as stainless steel.

A proximal end 34 of the stylet 14 includes a stylet retaining housing 36. The stylet retaining housing 36 is designed to secure the stylet 14 within the handle 12. Thus, the stylet retaining housing 36 is adapted to be contained within the ergonomic design of the cap 23. In addition, the stylet retaining housing 36 is retained within the handle 12 so that the stylet 14 cannot rotate while penetrating the bone cortex. In a preferred embodiment, the stylet retaining housing 36 is relatively square and is secured in a cooperating relatively square receiving cavity (not shown) within the handle 12.

The stylet 14 is adapted to be secured within the outer cannula 16 in order to penetrate the bone cortex. Thus, the outer diameter of the stylet 14 is slightly smaller than the inner diameter of the outer cannula 16. When the stylet 14 is inserted into the outer cannula 16 and the stylet retaining housing 36 is secured in the handle 12, the sharp distal tip 30 of the stylet 14 extends slightly beyond the distal tip 29 of the outer cannula 16, as seen in FIG. 1. Thus, the sharp distal tip 30 of the stylet 14 works in conjunction with the sharp distal tip 29 of the outer cannula 16 to assist in penetrating the bone cortex.

Figure 2B:
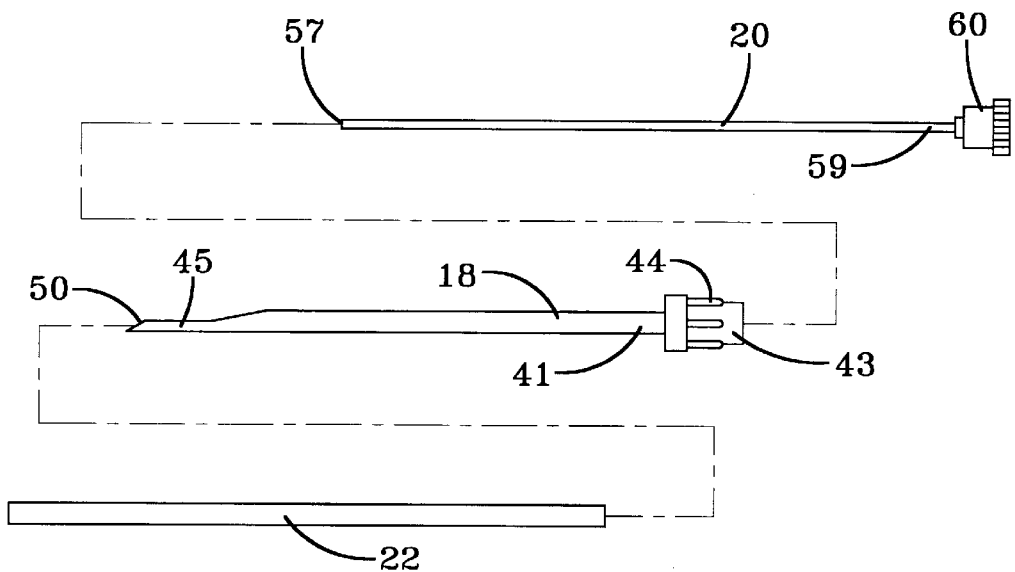
FIG. 2B is a perspective, exploded view of the inner member, the ejector pin, and the protective sheath of the bone marrow biopsy device of FIG. 1.

Referring now to FIG. 2B, the bone marrow biopsy device 10 made in accordance with the principles of the present invention also includes an inner member 18. A proximal end 41 of the inner member 18 is formed with a hub 43 that is secured to the inner member 18. The hub 43 includes a plurality of ribs 44 to aid in rotation of the hub 43 during use. A distal end of the inner member 18 defines a cutting finger 45. The width of the cutting finger 45 is preferably designed such that the cutting finger 45 is wide enough to maintain the structural integrity of the cutting finger 45 while being sufficiently narrow to avoid subjecting the tissue sample to compression forces.

Figure 3A:
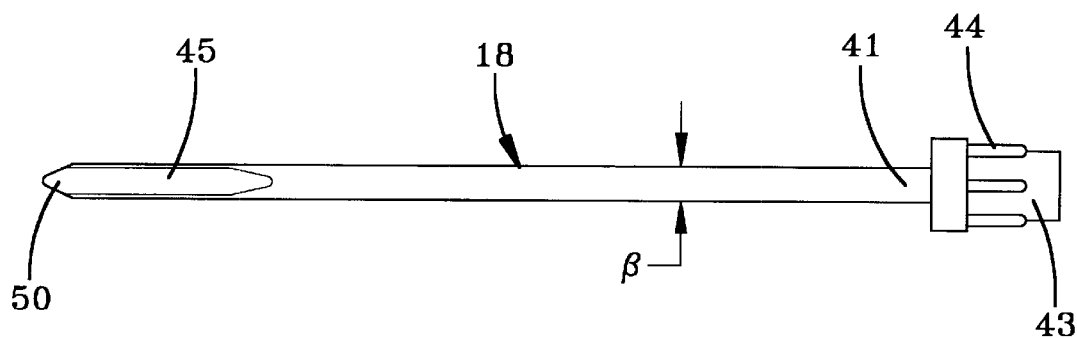
FIG. 3A is a close-up top view of the inner member showing the cutting finger of FIG. 2B.
Figure 3B:
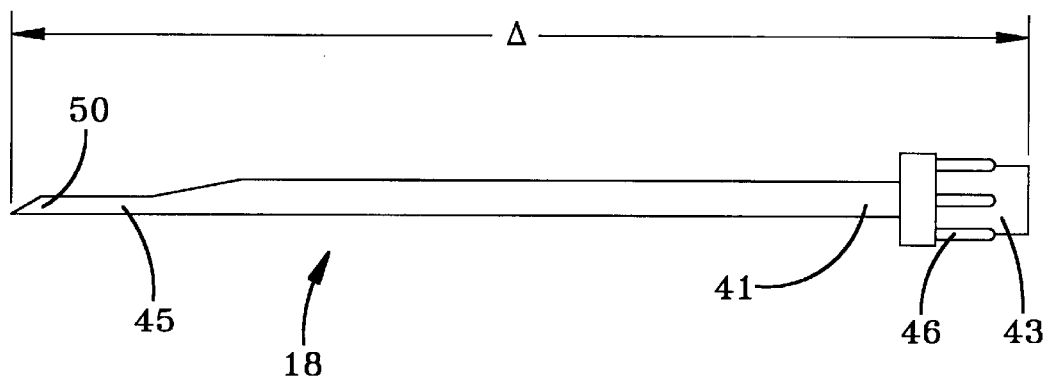
FIG. 3B is a close-up side view of the inner member showing the cutting finger of FIG. 2B.
Figure 4:
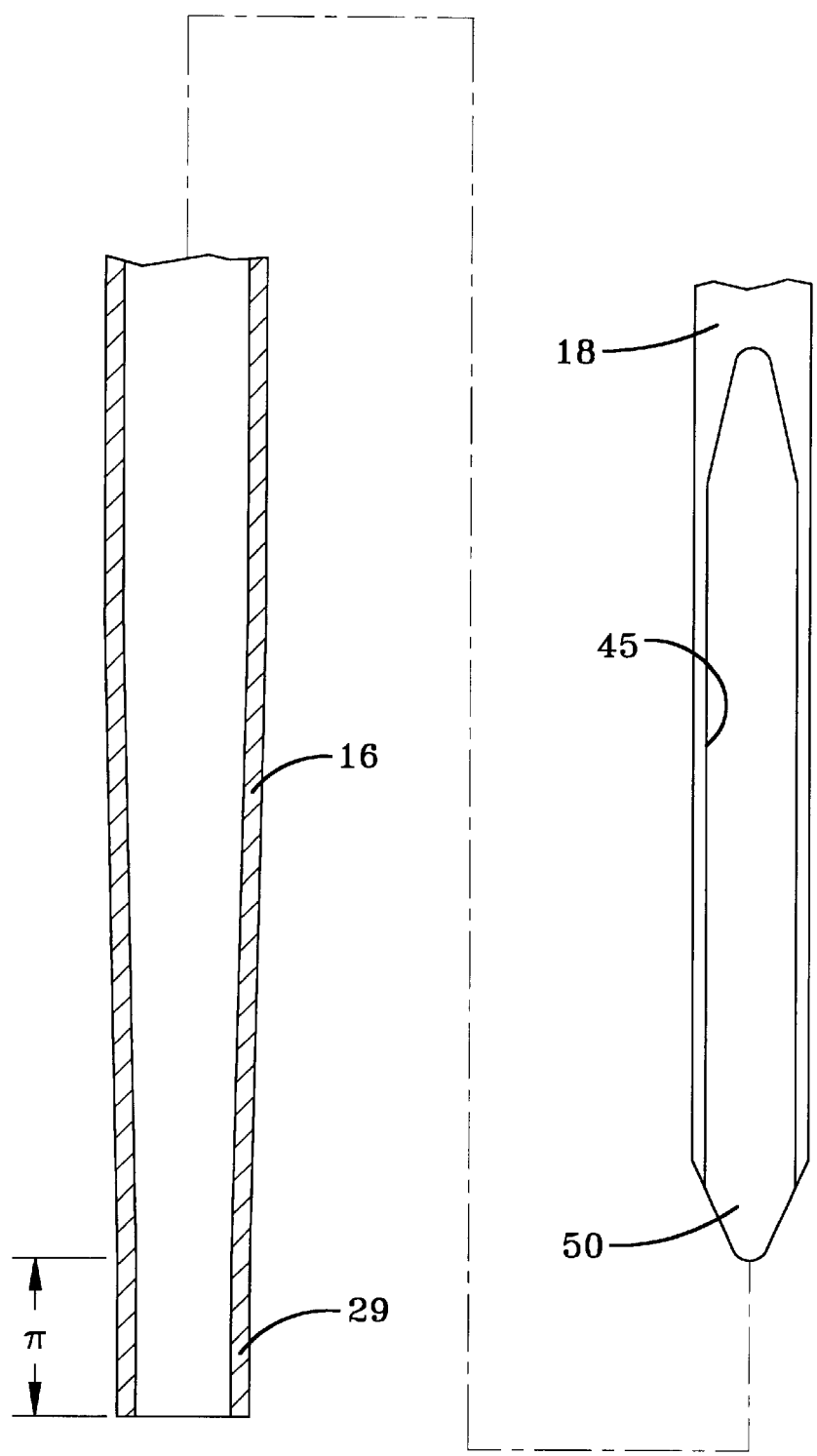
FIG. 4 is a close-up top view of the cutting finger of FIG. 3 and cross-sectional view of the outer cannula of FIG. 2.

Referring now to FIGS. 3 and 4, close-ups of the cutting finger 45 are seen. In a preferred embodiment, the width of the cutting finger 45 is approximately 60% of the circumference of the inner member 18. By cutting finger 45, it is met in an embodiment a blade-type member having generally sharp edges that is capable of cutting the tissue sample substantially from the bone marrow tissue without subjecting the tissue sample to undue compression forces and while being capable of structurally withstanding the force exerted on the blade. It has been found that if the cutting finger 45 is equal to or greater than about 60% of the circumference of the inner member 18, then the tissue sample is subjected to undue compression forces, thus causing undue tissue damage.

In one embodiment, the cutting finger is formed by grinding about at least 40% of the circumference of the inner member 18 away thereby forming a blade-type member having generally sharp edges. In addition, a distal tip 50 of the cutting finger 45 is beveled to facilitate cutting of the tissue sample. The taper of the distal tip 29 (seen in FIG. 2A) of the outer cannula 16 directs the cutting finger 45 inwardly. The inward extension of the cutting finger 45 causes the cutting finger 45 to sever the tissue sample from the tissue.

As seen in FIG. 2B, the bone marrow biopsy device 10 made in accordance with the principles of the present invention further includes an ejector pin 20. The ejector pin 20 is a solid piece designed to fit within the inner diameter of the inner member 18. A distal end 57 of the ejector pin 20 is blunt to avoid damaging the tissue sample when it is removed from the inner member 18. A proximal end 59 of the ejector pin 20 includes an ejector pin housing 60. The ejector pin housing 60 is designed to secure the ejector pin 20 within the inner member 18.

Finally, the bone marrow biopsy device 10 made in accordance with the principles of the present invention includes a protective sheath 22. The protective sheath 22 is designed to surround the inner member to protect the cutting finger 45 prior to use. In a preferred embodiment, the protective sheath 22 can be made from a plastic such as a low density polyethylene.

Referring now to FIG. 5, use of a bone marrow biopsy device 10 made in accordance with the principles of the present invention is described. The patient comprises outer skin layers 61, a periosteum layer consisting of layers of soft tissue 62, the hard cortex layer of the bone 64, and the medular cavity 66 which contains the bone marrow. In use, the stylet 14 is inserted into the outer cannula 16 and the stylet retaining housing 36 is locked into the handle 12. The health care professional then uses the sharp distal end of the stylet and the beveled distal end of the cannula to penetrate the bone cortex 64. Once the bone cortex 64 has been penetrated and the outer cannula is in the medular cavity 66, the stylet 14 is removed. The outer cannula 16 is then further inserted into the medular cavity 66, thereby trapping bone marrow tissue within the outer cannula 16.

In order to measure the size of the sample, the health care professional can insert the ejector pin 20 into the outer cannula 16. The length of the ejector pin 20 extending outward or proximally from the handle 12 estimates the length of the tissue sample. When an appropriate sample size has been selected, the inner member 18 is extended into the outer cannula 16. The inner member 18 cutting finger 45 slices through a small portion of the tissue sample, with the distal end of the cutting finger 45 extending to within a short distance ($\pi$) (seen in FIG. 4) from the distal end of the outer cannula 16. The taper of the distal tip 29 of the outer cannula 16 helps direct the cutting finger 45 inwardly towards the axis of the cannula. The inward extension of the cutting finger 45 helps the cutting finger 45 sever the tissue sample from the tissue.

After the inner member 18 has been fully inserted into the outer cannula 16, the health care professional rotates the inner member 18 by grasping and rotating the hub 43. During this rotation, the cutting finger 45 shears off the specimen while minimizing the amount of crushing effect on the tissue sample. The device 10 is then removed from the patient with the specimen contained within the distal portion of the inner member 18.

Referring now to FIGS. 6A and 6B, the inner member 18, the ejector pin 20, and the tissue sample 70 are seen after removal from the patient. In FIG. 6A the tissue sample 70 remains in the inner member 18. The ejector pin 20 can then be advanced through the inner member 18 to push the specimen out of the inner member 18, as seen in FIG. 6B.

INDUSTRIAL APPLICABILITY

Thus, the present invention meets a long-felt need in the medical community that has not been met by others to secure a large tissue sample while avoiding increasing the size of the biopsy device thereby minimizing the pain experienced by the patient during such procedure. The present invention further meets a long-felt need in the medical community that has not been met by others to avoid subjecting the tissue sample to undue forces, whether such forces be compression, suction, etc., thus reducing damage to the tissue following removal of the sample from the patient. The present invention surprisingly provides these and further advantages in a low-cost, easy-to-use device. .

It should be understood that various changes and modifications to the preferred embodiment described herein will be apparent to those skilled in the art. Such changes and modifications can be made without departing from the spirit and scope of the present invention and without demising its attendant advantages. It is therefore intended that such changes and modifications be covered by the appended claims.

What is claimed is:

1. A bone marrow biopsy device comprising:
    a handle;
    an outer cannula secured in the handle, the outer cannula defining a sharp distal tip that provides a distal cutting edge;
    a stylet designed to be inserted in the outer cannula, the stylet defining a sharp distal tip; and
    an inner member designed to be inserted in the outer cannula, the inner member defining a cutting finger comprising a pair of elongate blades adjacent a single elongate opening and structured to rotate relative to , and advance longitudinally within, the outer cannula to sever a specimen from surrounding tissue.

2. The bone marrow biopsy device of claim 1 further comprising an ejector pin designed to be inserted into the inner member.

3. The bone marrow biopsy device of claim 1 further comprising a protective sheath designed to surround the inner member.

4. The bone marrow biopsy device of claim 1 wherein the sharp distal tip of the stylet is designed to extend near to the distal tip of the outer cannula.

5. The bone marrow biopsy device of claim 1 wherein the cutting finger has a width designed such that the cutting finger is wide enough to maintain the structural integrity of the cutting finger while being sufficiently narrow to avoid subjecting a tissue sample to compression forces.

6. The bone marrow biopsy device of claim 5 wherein the width of the cutting finger is approximately 60% of the circumference of the inner member.

7. The bone marrow biopsy device of claim 5 wherein the cutting finger defines a distal tip that is beveled and the distal tip of the outer cannula is tapered such that the taper of the distal tip of the outer cannula directs the cutting finger inwardly when extended near to the outer cannula.

8. A member for use with a bone marrow biopsy device comprising:
   a proximal end formed with a hub that secures the member; and
   a distal end that defines a cutting finger comprising a pair of elongate blades adjacent a single elongate opening and structured to rotate relative to, and advance longitudinally within, other components of the bone marrow biopsy device to sever a specimen from surrounding tissue.

9. The member of claim 8 wherein the hub includes a plurality of ribs.

10. The member of claim 8 wherein the cutting finger has a width designed such that the cutting finger is wide enough to maintain the structural integrity of the cutting finger while being sufficiently narrow to avoid subjecting a tissue sample to compression forces.

11. The member of claim 10 wherein the width of the cutting finger is approximately 60% of the circumference of the member.

12. The member of claim 8 wherein the cutting finger defines a distal tip that is beveled.

13. A kit for use in obtaining a bone marrow biopsy comprising:
   a handle having an outer cannula secured therein, the outer cannula defining a distal tip that provides a distal cutting edge;
   a stylet designed to be inserted in the outer cannula, the stylet defining a sharp distal tip; and
   an inner member designed to be inserted in the outer cannula, the inner member defining a cutting finger comprising a pair of elongate blades adjacent a single elongate opening and structured to rotate relative to, and advance longitudinally within, to the outer cannula to serve a specimen from surrounding tissue.

14. The kit for use in obtaining a bone marrow biopsy of claim 13 further comprising an ejector pin designed to be inserted into the inner member.

15. The kit for use in obtaining a bone marrow biopsy of claim 13 further comprising a protective sheath designed to surround the inner member.

16. A method for sampling bone marrow tissue comprising:
   inserting a stylet into an outer cannula;
   penetrating the bone cortex with the stylet and the outer cannula;
   removing the stylet;
   further inserting the outer cannula into a medular cavity, thereby trapping bone marrow tissue within the outer cannula;
   extending an inner member into the outer cannula, the inner member defining a cutting finger comprising a pair of elongate blades adjacent a single elongate opening;
   rotating the inner member to advance longitudinally within and, relative to the outer cannula to shear off the specimen with the cutting finger; and removing the specimen from the patient.

17. The method for sampling bone marrow tissue of claim 16 wherein the step of penetrating the bone cortex with the stylet and the outer cannula is achieved by penetrating the bone cortex with a sharp distal end of the stylet and a beveled distal end of the cannula.

18. The method for sampling bone marrow tissue of claim 16 further including the step of estimating the length of tissue sample by inserting an ejector pin into the outer cannula after the outer cannula has been further inserted into the medular cavity.

19. The method for sampling bone marrow tissue of claim 16 further including the step of extending a distal end of the cutting finger near to a distal end of the outer cannula.

* * * * *